United States Patent [19]

Deason et al.

[11] 4,356,184
[45] Oct. 26, 1982

[54] ANTI-ALLERGIC OR ANTIHYPERTENSIVE 1-PIPERIDINYLMETHYL BENZENAMINES

[75] Inventors: James R. Deason, Wilmette; Richard A. Partis, Evanston, both of Ill.

[73] Assignee: G. D. Searle & Co., Skokie, Ill.

[21] Appl. No.: 247,568

[22] Filed: Mar. 25, 1981

Related U.S. Application Data

[63] Continuation-in-part of Ser. No. 156,248, Jun. 4, 1980, abandoned.

[51] Int. Cl.³ .................. A61K 31/445; C07D 409/04; C07D 211/14
[52] U.S. Cl. .................. 424/267; 546/202; 546/203
[58] Field of Search .................. 546/202, 203; 424/267

[56] References Cited

U.S. PATENT DOCUMENTS

| | | | |
|---|---|---|---|
| 3,014,911 | 12/1961 | Engelhardt | 546/203 |
| 3,862,156 | 1/1975 | Bourquin et al. | 546/202 |
| 4,275,209 | 6/1981 | Lassen et al. | 546/202 |

FOREIGN PATENT DOCUMENTS

| | | | |
|---|---|---|---|
| 746508 | 11/1966 | Canada | 546/203 |
| 2256392 | 5/1973 | Fed. Rep. of Germany | 546/202 |
| 1516783 | 3/1968 | France | 546/202 |
| 1103718 | 2/1968 | United Kingdom | 546/203 |

Primary Examiner—Richard A. Schwartz
Attorney, Agent, or Firm—James G. Passe

[57] ABSTRACT

1-Piperidinylmethyl benzenamines represented by the formula:

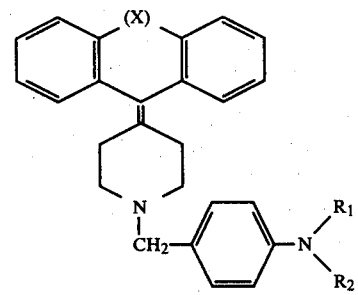

wherein X is S or —$CH_2$—$CH_2$—; $R_1$ and $R_2$ are the same different members of the group consisting of hydrogen or lower alkyl; and the pharmaceutically acceptable salts thereof. The compounds are useful as anti-allergic and antihypertensive agents.

8 Claims, No Drawings

ANTI-ALLERGIC OR ANTIHYPERTENSIVE 1-PIPERIDINYLMETHYL BENZENAMINES

This application is a continuation-in-part of Ser. No. 06/156,248, filed June 4, 1980 now abandoned.

FIELD OF THE INVENTION

The present invention relates to 1-piperidinylmethyl benzenamines which are useful as anti-allergic and anti-hypertensive agents.

SUMMARY

The 1-piperidinylmethyl benzenamines of the present invention are represented by Formula I:

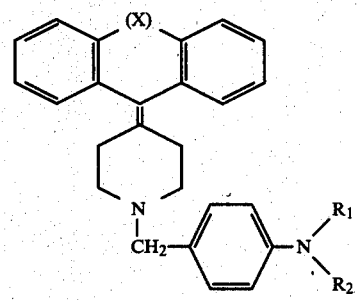

wherein X is S or —$CH_2$—$CH_2$—, and $R_1$ and $R_2$ are the same or different members of the group consisting of hydrogen or lower alkyl; and the pharmaceutically acceptable salts thereof.

The term "lower alkyl" as used herein, means a straight or branched chain alkyl radical of from 1 to 6 carbon atoms and includes, but is not limited to methyl, ethyl, n-propyl, isopropyl, n-butyl, iso-butyl, tert-butyl, n-pentyl, 2,2-dimethylpropyl, n-hexyl, etc.

The term "pharmaceutically acceptable salts" refers to the acid addition salts of the compounds of this invention prepared from any suitable organic or inorganic acid. Suitable salts include, for example: the hydrochloride, hydrobromide, sulfate, phosphate, acetate, propionate, oleate, lactate, napsylate, citrate, tartrate, succinate, fumarate, maleate, benzoate, etc. and the salts composed of 2 equivalents of the acid, e.g. the dihydrochloride.

The compounds of this invention are useful as anti-allergy and antihypertensive agents.

When X=S, the compounds of this invention are represented by Formula II:

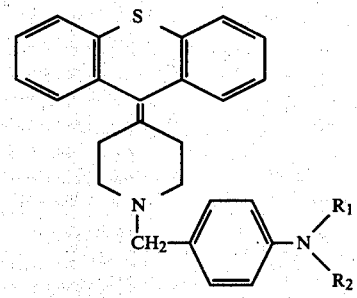

wherein $R_1$ and $R_2$ are as defined in Formula I.

When X is —$CH_2$—$CH_2$—, the compound of this invention are represented by Formula III:

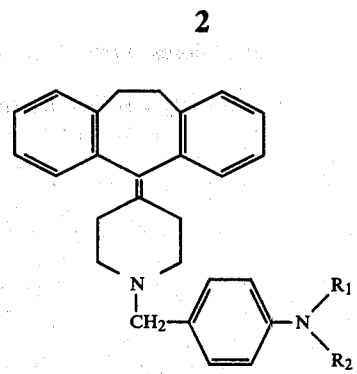

wherein $R_1$ and $R_2$ are as defined in Formula I.

Intermediates of Formula IV are also provided

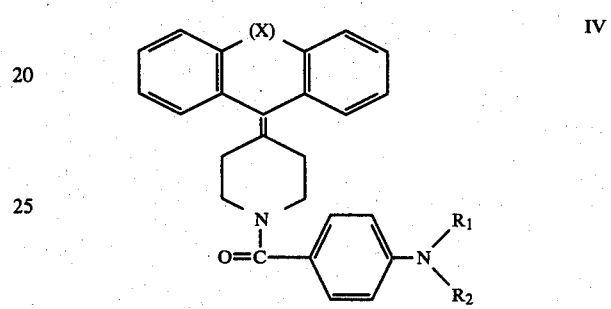

wherein X, $R_1$ and $R_2$ are as defined above.

DETAILED DESCRIPTION OF PREFERRED EMBODIMENTS

The preferred compounds of this invention are: N,N-dimethyl-4-{[4-(9H-thioxanthen-9-ylidene)-1-piperidinyl]methyl}benzenamine(X=S, Compound I) and N,N-dimethyl-4-{[4-(5H-dibenzo[a,d]cycloheptan-5-ylidene)-1-piperidinyl]methyl}benzenamine. X=—$CH_2$—$CH_2$, Compound 2).

The compounds of this invention can be administered orally or parenterally, i.e., intravenously, intramuscularly or intraperitoneally, and may be administered alone or admixed with one or more suitable pharmaceutically acceptable carriers or diluents.

The anti-allergy activity of compounds of this invention was first determined in the passive cutaneous anaphylaxis anti-allergy screen in rats, conducted generally as follows. Fasted, male rats weighing 200-250 grams were passively skin sensitized with immunoglobulin E (IgE) specific for ovalbumin (OA). Forty-eight hours later, the rats were challenged by intravenous injection of ovalbumin and Evans blue dye, having received test compound or control one hour prior to OA challenge. The diameter of the blue spots created by the discrete IgE concentration-dependent areas of permeability were measured 30 minutes post challenge. In allergic states, this same mediator release mechanism is activated upon exposure to the antigen to which the person is allergic and allergic symptomatology follows including urticaria, rashes, bronchoconstriction, etc. Compounds causing causing a statistically significant reduction P($\leq 0.05$) in size of the passive cutaneous anaphylaxis skin reaction in treated rats versus controls is rated as active.

Compound I exhibited anti-allergy activity at oral doses of from 0.2 to 50 mg/kg and Compound 2 exhibited anti-allergy activity at doses of from 5 to 50 mg/kg on the above assay.

The antihypertensive activity was first determined in the spontaneously hypertensive rat assay conducted generally as follows. An initial intragastric dose of 50 mg/kg was administered to male, 11–16 week old spontaneously hypertensive rats, obtained from Laboratory Animal Supply Co., Indianapolis, Ind., 46241, after maintaining them for at least 1 week in-house before use. Initial blood pressure was measured by a caudal plethysmograph immediately before administration of test compound. Blood pressure readings were repeated 4 and 24 hours after administration of the test compound. Compound 1 significantly reduced blood pressure in the spontaneously hypertensive rat at oral doses of 24 and 50 mg/kg and Compound 2 at oral doses of from 12.5 to 50 mg/kg.

The dosage and route of administration will vary depending upon the patient and the route of administration. Known compound cyproheptadine has a minimum effective dose in the above anti-allergy rat screen of 5 mg/kg. In humans cyproheptadine has an effective dosage down to 0.06 mg/kg. Based on the results of the anti-allergy rat screen, the invention compounds therefore would be effective anti-allergy agents in humans at a dosage range from about 0.01 to 2 mg/kg and preferably from about 0.02 to 0.1 mg/kg. In addition, the compounds are active to lower blood pressure in hypertensive patients at a dosage from about 12.5 to 50 mg/kg and preferably from about 12.5 to 15 mg/kg.

The following examples further illustrate the present invention.

EXAMPLE 1

Preparation of [4-(dimethylamino)phenyl][4-(9-H-thioxanthen-9-ylidene)-1-piperidinyl]methanone To a magnetically stirred, ice-cooled solution of p-dimethylaminobenzoyl chloride (0.02 mole) and triethylamine (20 ml) in methylene chloride (300 ml) under an argon atmosphere was added dropwise a solution of 4-(9-thioxanthylidene)-piperidine (0.0133 mole) in methylene chloride (100 ml) over a twenty minute period. After stirring for 48 hours at room temperature, water (250 ml) was added and the mixture stirred for an additional 30 minutes. The layers were separated and the organic layer was washed with water (100 ml), 5% sodium hydroxide (2×200 ml) and water (250 ml), and then dried over sodium sulfate, filtered and stripped under reduced pressure to a dark orange oil. The product was purified by low pressure column chromatography using a 25×1000 mm column packed with 250 g. of silica gel absorbent and eluted with ethyl acetate to yield 2.3 grams of the product. Recrystallization from toluene yielded 2.1 g. of product, m.p. 178°–186° C. (decomp.)

Analysis Calcd. for $C_{27}H_{26}N_2OS$: C, 76.02; H, 6.14; N, 6.57; S, 7.52. Found: C, 75.97; H, 6.27; N, 6.46; S, 7.48.

EXAMPLE 2

Preparation of N,N-dimethyl-4-{[4-(9H-thioxanthen-9-ylidene)-1-piperidinyl]methyl benzenamine} dihydrochloride To an ice cooled solution of aluminum hydride (0.02 mole) in tetrahydrofuran (85 ml) under an atmosphere of argon was added a solution of the amide of Example 1 (0.0044 moles) in tetrahydrofuran (40 ml) dropwise over over 30 minutes. After stirring at room temperature for 64 hours, water (1.5 ml) was added slowly followed by the addition of 12.5% sodium hydroxide (1.5 ml) and then water (1.5 ml). After stirring for 30 minutes the aluminum salts were filtered by reduced pressure and washed with tetrahydrofuran (100 ml). The combined filtrate and wash was dried over sodium sulfate for 60 minutes, filtered by suction and stripped under reduced pressure to give an oil. The oil was dissolved in diethyl ether (350 ml) and filtered through Celite. To this rapidly stirring solution was added dropwise a saturated solution of hydrogen chloride gas in isopropyl alcohol until no further precipitate was formed. The white solid was filtered off, washed with diethyl ether (50 ml) and dried in a vacuum desiccator overnight. The solid was recrystallized from ethanol Skellysolve B to yield 1.23 g. of product; m.p. 205°–207° C.

Analysis Calcd. for $C_{27}H_{30}N_2Cl_2S$: C, 66.79; H, 6.23; N, 5.77; S, 6.60; Cl, 14.60. Found C, 66.79; H, 6.17; N, 5.73; S, 6.69; Cl, 14.32.

EXAMPLE 3

Preparation of [4-(10,11-dihydro-5H-dibenzo[a,d]cycloheptan-5-ylidene)-1-piperidinyl][4-(dimethylamino)phenyl]methanone A solution of 4(5H-dibenzo[a,d]cycloheptane-5-ylidene)piperidine (0.027 moles) and triethylamine (25 ml) in methylene chloride (500 ml) was added slowly over 1.5 hours to an ice cooled solution of p-dimethylaminobenzoyl chloride (0.041 moles) in methylene chloride (500 ml). After stirring at room temperature overnight, water (300 ml) was added and the resulting mixture was stirred for 1 hour. The layers were separated and the organic phase was washed with water (300 ml), 5% sodium hydroxide (2×400 ml) and water (500 ml), dried over sodium sulfate for 1 hour, filtered by suction and stripped under reduced pressure to an orange-red oil. The oil crystallized from toluene (300 ml) and skellysolve B (300 ml). The two crops obtained were combined (wt 12 g.), dissolved in toluene and clarified with Norit (2 g.). After filtering off the Norit and reducing the volume to approximately ½ (nitrogen flush), the solution was placed in the refrigerator, and the resulting mixture was filtered to give 9.3 g. of a solid.

1 g. of the solid was recrystallized from toluene to yield 0.56 g. of product, m.p. 181°–184.5° C. (decomp)

Analysis Calcd. for $C_{29}H_{30}N_2O$: C, 82.43; H, 7.16; N, 6.63. Found C, 82.61; H, 7.26; N, 6.44.

EXAMPLE 4

Preparation of 4-{[4-(10,11-dihydro-5H-dibenzo[a,d]cycloheptan-5-ylidene)-1-piperidinyl]methyl}-N,N-dimethylbenzenamine dihydrochloride To an ice cooled solution of aluminum hydride (0.09 moles) in tetrahydrofuran (110 ml) was added slowly (1 hour) a solution of the compound of Example 3 (0.0196 moles) in tetrahydrofuran (100 ml). After stirring at room temperature for 20 hours, a solution of water (3.5 ml) in tetrahydrofuran (10 ml) was added dropwise followed by the addition of 12.5% sodium hydroxide (3.5 ml) and then water (20 ml). After stirring for 30 minutes the aluminum salts were filtered by suction and the filtrate stripped under reduced pressure to an oil. The aluminum salts were washed well with hot diethyl ether (2×500 ml) and added with water (100 ml) to the above oil. After stirring the layers for 30 minutes, the layers were separated and the aqueous layer was washed with methylene chloride (50 ml). The diethyl ether layer and methylene chloride washes were combined and dried over sodium sulfate for 30 minutes and then the dihydrochloride salt was prepared by adding a saturated solution of hydrogen chloride gas in isopropyl alcohol slowly until no further precipitate formed. The white solid was collected by filtration and washed well with diethyl ether (200 ml). The solid was recrystallized from water-acetone yielding 5.1 g. of product, m.p. 234°–236.5° C.

Analysis Calcd. for $C_{29}H_{34}N_2Cl_2$: C, 72.33; H, 7.12; N, 5.82; Cl, 14.73. Found C, 72.63; H, 7.18; N, 5.82; Cl, 14.64.

It will be understood by those skilled in the art that the above examples are given by way of illustration, and it is obvious that the following illustrative compounds can be readily synthesized by approximately varying the starting materials:

4-[4-(9H-thioxanthene-9-ylidene)-1-piperidinylmethyl]benzenamine

N-methyl-4-[4-(9H-thioxanthene-9-ylidene)-1-piperidinylmethyl]benzenamine

N-ethyl-4-[4-(9H-thioxanthene-9-ylidene)-1-piperidinylmethyl]benzenamine

N,N-diethyl-4-[4-(9H-thioxanthene-9-ylidene)-1-piperidinylmethyl]benzenamine

N-n-propyl-4-[4-(9H-thioxanthene-9-ylidene)-1-piperidinylmethyl]benzenamine

N,N-di-n-propyl-4-[4-(9H-thioxanthene-9-ylidene)-1-piperidinylmethyl]benzenamine N-iso-propyl-4-[4-(9H-thioxanthene-9-ylidene)-1-piperidinylmethyl]benzenamine N-n-di-n-butyl-4-[4-(9H-thioxanthene-9-ylidene)-1-piperidinylmethyl]benzenamine 4-[4-(5H-dibenzo[a,d]cycloheptan-5-ylidene)-1-piperidinylmethyl]benzenamine N-methyl-4-[4-(5H-dibenzo[a,d]cycloheptan-5-ylidine)-1-piperidinylmethyl]benzenamine N-ethyl-4-[4-(5H-dibenzo[a,d]cycloheptan-5-ylidine-1-piperidinylmethyl]benzenamine N,N-diethyl-4-[4-(5H-dibenzo[a,d]cycloheptan-5-ylidine-1-piperidinylmethyl]benzenamine N-n-propyl-4-[4-5H-dibenzo[a,d]cycloheptan-5-ylidine)-1-piperidinylmethyl]benzenamine, etc.

The compounds of this invention can be administered by oral or parenteral routes of administration and can be formulated in dosage forms appropriate for each route of administration.

Solid dosage forms for oral administration include capsules, tablets, pills, powders and granules. In such solid dosage forms, the active compound is admixed with at least one inert diluent such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides, inert diluents, such compositions can also include adjuvants, such as wetting agents, emulsifying and suspending agents, and sweetening, flavoring, and perfuming agents.

Preparations according to this invention for parenteral administration include sterile aqueous or non-aqueous solutions, suspension, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 0.01 to 50 mg/kg of body weight daily are administered to mammals to obtain effective relief from allergic reactions or to treat hypertension.

The following example further illustrates the pharmaceutical compositions which are a feature of this invention.

EXAMPLE 5

Tablets weighing 200 mg. and having the following compositions are formulated:

| Ingredient | Mg |
|---|---|
| N,N—dimethyl-4-{[4-(9H—thioxanthen-9-ylidene)-1-piperidinyl]methyl benzenamine} dihydrochloride | 25 |
| Starch | 145 |
| Colloidal silica | 27 |
| Magnesium stearate | 3 |

We claim:
1. A 1-piperidinylmethyl benzenamine represented by the formula:

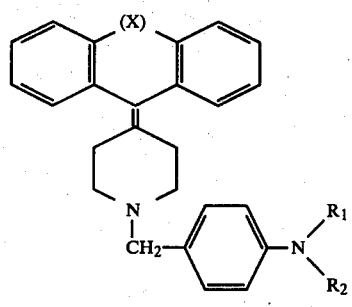

wherein: X is —S— or —CH$_2$—CH$_2$—; and R$_1$ and R$_2$ are the same or different members of the group consisting of hydrogen or loweralkyl; or a the pharmaceutically acceptable salt thereof.

2. A compound of claim 1 wherein X is —S— and the compound is represented by the Formula:

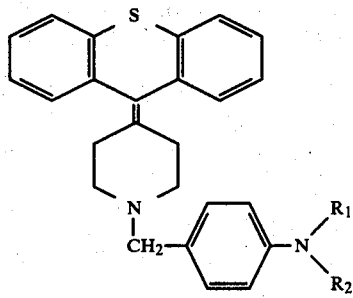

wherein R₁ and R₂ are as defined in claim 1.

3. A compound of claim 2; N,N-dimethyl-4-[4-(9H-thioxanthene-9-ylidene)-1-piperidinylmethyl]-benzenamine or a pharmaceutically acceptable salt thereof.

4. A compound of claim 1 wherein X is —CH₂—CH₂— and the compound is represented by the formula

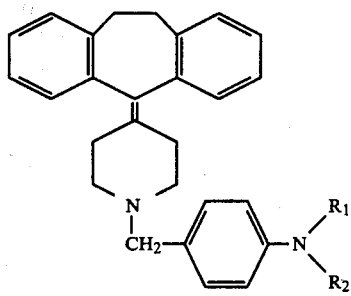

wherein R₁ and R₂ are as defined in claim 1.

5. A compound of claim 4: N,N-dimethyl-4-[4-(5H-dibenzo[a,d]cycloheptan-5-ylidene)-1-piperidinylmethyl]benzenamine or a pharmaceutically acceptable salt thereof.

6. An anti-allergic or antihypertensive pharmaceutical composition comprising a therapeutically effective amount of a compound of claim 1 and a pharmaceutically acceptable carrier or diluent.

7. A pharmaceutical composition of claim 6 wherein said compound is N,N-dimethyl-4-[4-(9H-thioxanthene-9-ylidine)-1-piperidinylmethyl]-benzenamine or a pharmaceutically acceptable salt thereof.

8. A pharmaceutical composition of claim 6 wherein said compound is N,N-dimethyl-4-[4-(5H-dibenzo[a,d]cycloheptan-5-ylidene-1-piperidinylmethyl]benzenamine or a pharmaceutically acceptable salt thereof.

* * * * *